United States Patent [19]
Roos et al.

[11] Patent Number: 6,041,097
[45] Date of Patent: Mar. 21, 2000

[54] METHOD AND APPARATUS FOR ACQUIRING VOLUMETRIC IMAGE DATA USING FLAT PANEL MATRIX IMAGE RECEPTOR

[75] Inventors: Pieter Gerhard Roos, Bainbridge; Andrew J. Ivan, Aurora; Rodney A. Mattson, Mentor, all of Ohio

[73] Assignee: Picker International, Inc., Highland Heights, Ohio

[21] Appl. No.: 09/055,607

[22] Filed: Apr. 6, 1998

[51] Int. Cl.$^7$ .............................. G01N 23/04; A61B 6/03
[52] U.S. Cl. .................................... 378/62; 378/4; 378/19
[58] Field of Search .................. 378/4, 15, 19, 378/62, 98.8, 901

[56] References Cited

U.S. PATENT DOCUMENTS

| | | | |
|---|---|---|---|
| 4,352,986 | 10/1982 | Pfeiler ........................................ | 378/14 |
| 4,442,489 | 4/1984 | Wagner ..................................... | 378/19 |
| 4,810,881 | 3/1989 | Berger et al. ....................... | 250/370.01 |
| 5,287,274 | 2/1994 | Saint Felix et al. ...................... | 378/13 |
| 5,452,337 | 9/1995 | Endo et al. ................................. | 378/4 |
| 5,592,523 | 1/1997 | Tuy et al. ................................ | 378/19 |
| 5,625,660 | 4/1997 | Tuy .......................................... | 378/15 |
| 5,912,943 | 6/1999 | Deusher et al. ....................... | 378/98.8 |

FOREIGN PATENT DOCUMENTS

| | | |
|---|---|---|
| 0 471 455 A2 | 7/1991 | European Pat. Off. . |
| 2 088 670 | 11/1980 | United Kingdom . |

OTHER PUBLICATIONS

Amorphous Silicon X–Ray Image Sensor, J. Chabbal, et al. No Date.

An Image Intensifier–Based Volume Tomographic Angiography Imaging System, Ruola Ning, et al., SPIE vol. 3023, Feb. 23–25, 1997, San Jose, California.

3D X–Ray Angiography: Study of Factors Affecting Projection Data Consistency, Hsiang–Hsin Hsiung, et al., SPIE vol. 3032, Feb. 23–25, 1997, San Jose, California.

*Primary Examiner*—David V. Bruce
*Attorney, Agent, or Firm*—Fay, Sharpe, Fagan, Minnich & McKee, LLP

[57] ABSTRACT

A gantry (10) includes a large diameter bearing having an outer race (12) and an inner race (16) which surrounds an examination region. An x-ray tube (18) and collimator (52) are mounted to the inner race, as is a flat panel detector (20) and a mechanical mechanism (50) for moving the flat panel detector closer to and further from the examination region. A timing and control circuit (30) controls a motor (22) which indexes the inner race around the examination region, an x-ray power supply (32) which pulses the x-ray tube in a fluoroscopic mode at discrete positions around the examination region, and a read out circuit (34) which reads out a frame of data after each pulse of the x-ray tube. The read out frames of data are stored in a frame memory (36) and reconstructed by a reconstruction processor (38) into a volumetric image representation for storage in a volume image memory (40). A video processor (42) reformats individual frames from frame memory (36) or selected portions of volume image representation from the volume image memory (40) into appropriate format for display on a video monitor (44). A magnification control (54) coordinates adjustment of the collimator (52) and movement of the flat plate detector toward and away from the examination region.

27 Claims, 2 Drawing Sheets

METHOD AND APPARATUS FOR ACQUIRING VOLUMETRIC IMAGE DATA USING FLAT PANEL MATRIX IMAGE RECEPTOR

BACKGROUND OF THE INVENTION

The present invention relates to the medical diagnostic imaging arts. It finds particular application in conjunction with computerized tomographic (CT) scanners and fluoroscopy systems and will be described with particular reference thereto. However, it should be appreciated that the present invention may also find application in conjunction with other types of imaging systems and applications where volumetric imaging data is acquired.

Conventional, single detector ring, axial computerized tomography (CT), and its extensions, such as spiral CT and multiple detector ring CT, are well known and documented. In all these cases, multiple individual radiation detector elements, or small arrays of detector elements, are mounted on an inside cylindrical surface of the gantry, to form one (in the case of conventional CT), or a small number of rings (in the case of multi-slice CT). In some scanners the detectors are mounted on arc segments that rotate with the gantry.

An x-ray source emits a thin, highly collimated x-ray fan beam. Rotation of the gantry is typically continuous, with one or a few CT slices acquired with each revolution. Data from larger volumes are acquired by either indexing the patient in steps, synchronized with the gantry rotation (in the case of conventional CT), or continuously (in the case of spiral CT), along the center line of rotation and acquiring one or a few CT slices with each revolution.

Alternatively, volume CT data has been acquired with limited success, by mounting image intensifier-based fluoroscopic cameras on CT-gantry type frames. Such a system is described in a paper presented at SPIE Medical Imaging Conference on Feb. 24, 1997, by R. Ning, X. Wang and D. L. Conover of Univ. of Rochester Medical Center. The major disadvantage of this approach lies in the geometric distortion inherent to image intensifiers. Before a volume CT reconstruction can be performed, all video data has to be processed through an extremely tedious geometric correction algorithm, and even this is only partially successful, as the geometric distortion is typically dependent on the orientation, in space, of the image intensifier and thus the distortion pattern changes as the gantry rotates.

Further disadvantages of this concept lie in the veiling glare characteristic of image intensifiers, which reduces object contrast and causes reconstruction artifacts, and in the poor spatial resolution of image intensifiers. Because of the difficulty of reconstructing volume CT from image intensifier image data, and also because of the size and weight of image intensifier cameras, practical application of this concept has been virtually non-existent.

U.S. Pat. No. 5,588,033 discloses a third method for acquiring volume CT data, which involves the use of individual sheets of photographic film to acquire images at a series of angles through a patient. This method overcomes the limitations of image intensifier geometric distortion, but is extremely cumbersome due to the need to take individual photographic images that have to be developed and scanned into a computer for CT reconstruction processing. In practice, this limits the number of projections that can be acquired per examination, and thus limits the quality of CT image data that can be obtained. Such a procedure also takes a long time, during which the patient has to remain completely stationary.

Accordingly, it has been considered desirable to develop a new and improved method and apparatus for acquiring volumetric computer tomography image data using a flat panel matrix image receptor which meets the above-stated needs and overcomes the foregoing difficulties and others while providing better and more advantageous results.

SUMMARY OF THE INVENTION

In accordance with one aspect of the present invention, a fluoroscopic diagnostic imaging device is disclosed. The fluoroscopic diagnostic imaging device includes a gantry which supports an x-ray tube and a flat plate x-ray detector for rotation about an examination region with the x-ray tube and the flat plate detector disposed across the examination region from each other. A motor assembly selectively rotates the x-ray tube and the flat plate detector around the examination region. A read out device reads a two dimensional array of data values from the flat plate detector with each data value being indicative of radiation attenuation along one of a number of diverging rays extending between the x-ray source and a sub-region of the flat plate detector. A processor reconstructs the data values read out during rotation of the x-ray tube and the flat plate detector around the examination region into a volumetric image representation. A video processor formats (i) the read out data values into appropriate format for display on a video monitor as a projection image, and (ii) reformats selective portions of volumetric image data into an appropriate format for display on the monitor.

In accordance with another aspect of the present invention, a method of diagnostic imaging with a fluoroscopic imaging system is disclosed. The diagnostic imaging system includes a fluoroscopic imaging system having a gantry which supports an x-ray tube and a flat plate x-ray detector disposed across an examination region from each other, and a reconstruction processor for processing image data acquired by the flat plate x-ray detector. The method includes a) rotating the x-ray tube and the flat plate detector to a predetermined angular position about the examination region, b) energizing the x-ray tube to generate an x-ray radiation beam, c) reading out a two-dimensional array of data values from the flat plate detector with each data value being indicative of radiation attenuation along one of a plurality of diverging rays extending between the x-ray source and a sub-region of the flat plate detector, d) repeating steps (a–c) a predetermined number of times to collect a plurality of two dimensional arrays of data values, e) reconstructing the plurality of two-dimensional arrays of data values into a volumetric image representation, and f) displaying the volumetric image representation on a video monitor as a projection image.

One advantage of the present invention is the provision of a volumetric image data acquisition system which improves x-ray utilization resulting in lower power operation, longer x-ray tube life, faster patient scan times and reduced radiation dose.

Another advantage of the present invention is the provision of a volumetric image data acquisition system which improves spatial resolution due to the fine detector matrix spacings achievable in flat panel matrix image receptor technology.

Yet another advantage of the present invention is the provision of a volumetric image data acquisition system which acquires a large number of slices per gantry revolution resulting in reduced revolution speeds, but with faster patient scan times.

Still another advantage of the present invention is the provision of a volumetric image data acquisition system which reduces gantry complexity.

Still another advantage of the present invention is the provision of a dual-mode volumetric image data acquisition system which generates fluoroscopic image representations and radiographic image representations. In particular, the dual-mode volumetric image date acquisition system can be defined as a volume CT system that can also be used as a fluoroscopic system, or a fluoroscopic system that can be used as a volume CT system.

Still further advantages of the present invention will become apparent to those of ordinary skill in the art upon reading and understanding the following detailed description of the referred embodiments.

BRIEF DESCRIPTION OF THE DRAWINGS

The invention may take form in various components and arrangements of components, and in various steps and arrangements of steps. The drawings are only for purposes of illustrating a preferred embodiment(s) and are not to be construed as limiting the invention.

DETAILED DESCRIPTION OF THE PREFERRED EMBODIMENTS

Figure 1:
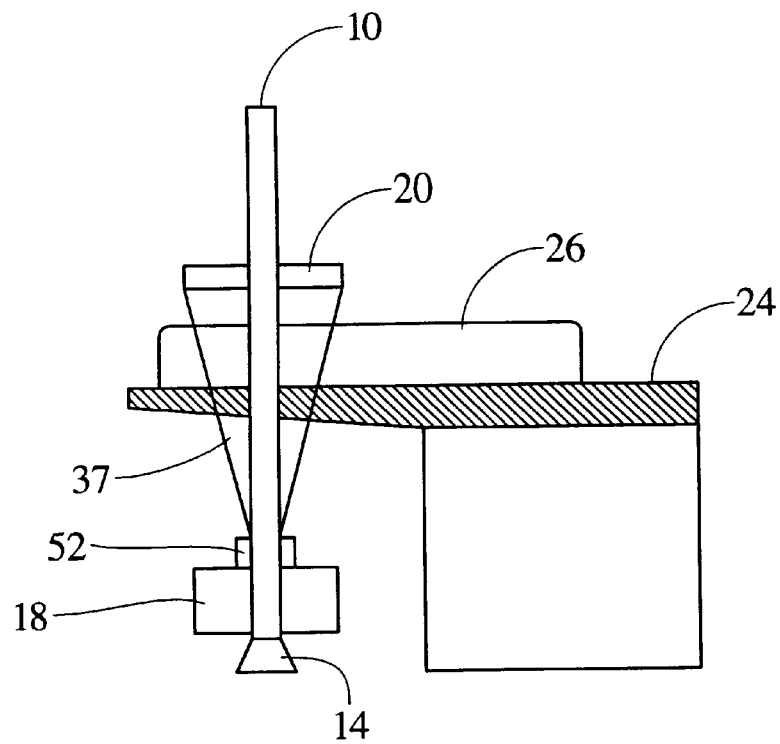
FIG. 1 is a diagrammatical side elevation view of an imaging apparatus which incorporates the features of the present invention therein.
Figure 2:
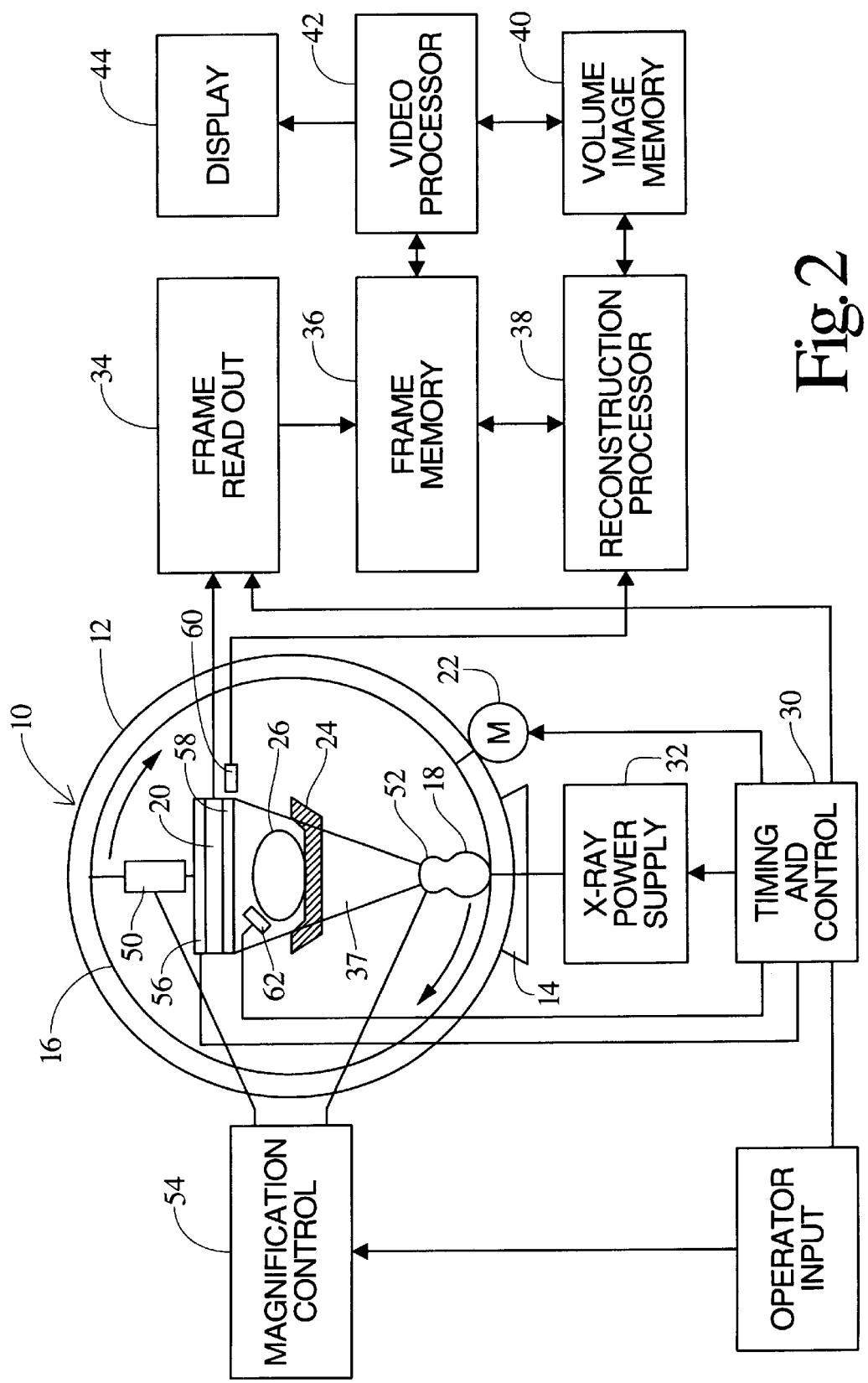
FIG. 2 is a simplified block diagram of the imaging apparatus of FIG. 1.

With reference to FIGS. 1 and 2, a large diameter track 10, on the order of 1.5 meters, is stationarily mounted to the floor. More specifically to the illustrated embodiment, the track is a large diameter bearing whose outer race 12 is stationarily supported by a stationary support 14 and whose inner race 16 is freely rotatable within the outer race. An x-ray tube 18 is mounted to the inner race for rotation therewith. A flat panel detector 20 is mounted to the inner race opposite the x-ray source. More specifically to the preferred embodiment, the flat panel detector includes a two dimensional matrix image receptor configured of a single, large amorphous silicon flat panel on the order of 30×40 centimeters. Suitable amorphous silicon flat panel image receptors are described in U.S. Pat. Nos. 5,079,426; 5,117, 114; 5,164,809; 5,262,649.

A drive motor 22 is connected with the inner race for indexing the x-ray tube and flat panel detector to selectable angular orientations around a central axis of the ring 10. A patient support 24 is positioned to support a region of interest of a subject 26 at the geometric center of the ring 10.

A timing and control circuit 30 controls the motor 22 to index the x-ray tube to each of a plurality of pre-selected angular positions around the subject, e.g., steps at 1° intervals. At each step, the timing and control circuit causes an x-ray tube power supply 32 to pulse the x-ray tube at radiographic energy levels in a radiographic mode of operation, and fluoroscopic energy levels in a fluoroscopic mode of operation. The x-ray tube sends a pulse of x-rays for a limited duration through the subject striking the flat panel detector 10. Due to the low fluoroscopic energy levels, each cell of the flat panel detector integrates received radiation over the duration of the pulse. After the radiation pulse, the timing and control circuit 30 causes a frame read out circuit 34 to read out the two dimensional frame image generated by the flat panel detector 20. Concurrently, the timing and control circuit causes the motor 22 to index the x-ray tube and flat panel detector to the next angular step.

This process is repeated to collect a plurality of two dimensional image frames which are collected in a frame memory 36. Each frame image includes a two dimensional array of data which represents radiation attenuation along a corresponding ray through the patient. Because the x-ray tube is essentially a point source which generates rays of diverging radiation directed toward the flat panel receptor, each ray represents the attenuation of radiation along one of a plurality of diverging paths. The paths diverge generally in a cone beam pattern 37. A cone beam reconstruction processor 38 reconstructs each frame of data and uses it to improve the three dimensional volumetric image that is built in a volumetric image memory 40. Various cone beam reconstruction algorithms are contemplated, such as described in U.S. Pat. Nos. 5,170,439; 5,404,293; 5,532, 490; 5,559,335; 5,565,684; and 5,625,660. With each frame that is reconstructed and combined into the volumetric image representation, the volumetric image becomes clearer and sharper. Preferably, the x-ray source and flat panel detector rotate at least 180° plus the angle of the cone beam and the rotational direction around the subject.

A video processor 42 addresses the volume image memory to retrieve slices, projections, 3-D renderings, and other conventional diagnostic image display formats such as Maximum Intensity Projection images (MIP).

The resolution and size of the acquired image data is adjustable by adjusting the displacement of the flat panel detector from the subject. More specifically, a mechanical drive 50 moves the flat panel detector 20 toward and away from a subject. Analogously, a collimator 52 adjusts the collimation or divergence of the fan beam of radiation generated by the x-ray tube to limit or block that portion of the radiation beam that will not impinge directly upon or strike the flat panel detector. A magnification control 54 is connected with the collimator 52 and the flat panel drive 50 to adjust the two in coordination such that the x-ray tube projects a fan beam which infringes on the flat panel detector, without sending rays of radiation to the sides of the detector. Such radiation rays which do not strike the detector, are blocked by the collimator 52 so as not to subject the object or patient 26 to radiation which does not contribute to the resultant image. By moving the flat plate detector close to the subject, a relatively large volume of the subject can be examined. By moving the flat panel detector away from the subject and narrowing the collimation a relatively small region of the subject can be reconstructed, with higher resolution.

The gantry 10 rotates at significantly reduced speed; approximately 5 to 90 seconds per revolution, versus 0.5 to 4 seconds per revolution for a conventional CT. In each rotation, 3–500 images are generated. Image data from the flat panel detector 20 and power to the x-ray source 18 may be transmitted from a continuously rotatable gantry 10 to the fixed frame 12 by conventional sliprings (not shown).

However, since sufficient data for most medical examinations can be acquired from a half or one complete revolution, data and power transfer can also be accomplished with slack power and data cables to the gantry 10. Alternatively, power and data can be stored on the gantry 10, with downloading of data and recharge of power storage at a docking station at the end of each revolution. In either case, three-dimensional image data can be acquired from the whole volume irradiated by the x-ray cone beam in a single revolution.

Rather than supporting the flat panel detector 20 and x-ray tube 18 with their geometric centers in the central plane of the gantry 10, as shown in FIGS. 1 and 2, the detector 20 and x-ray tube 18 can be supported in a cantilever manner, outside the gantry plane. This improves the physician's access to the patient during interventional procedures. A cantilevered mounting approach is feasible in part because of the relatively light weight of the flat panel image receptor 20 relative to a conventional image intensifier, and of the x-ray source, because of the lower x-ray power requirement. The slower scan speed of the gantry 10 also reduces safety problems associated with a cantilever mounting approach.

It should be appreciated that the two-dimensional flat panel image detector 20 utilizes a much larger fraction of all the x-rays produced by the x-ray tube 18 relative to a conventional CT detector technology. In addition, flat panel imagers have higher spatial resolution than conventional CT detectors or fluoroscopic imagers. This higher spatial resolution can be utilized either to acquire higher resolution images, or to place the detector closer to the gantry rotation axis, thus needing a smaller detector. In addition, flat panel image receptors are free from geometric distortion that has thus far precluded the practical use of fluoroscopic image intensifiers as detectors in volume CT. Further, flat panel image receptors have a much higher dynamic range than image intensifier implementations as the detector for volume CT, and flat panel image receptors are free from the veiling glare characteristic of image intensifiers, thus providing object contrast and no glare artifacts, which is a significant advantage over image intensifier based designs.

The flat panel image detector 20 can be optimized to acquire volume image data. For instance, by using a sensor 20 with significantly larger pixels than the pixels used in fluoroscopic sensors, it is possible to increase the dynamic range of the sensor 20 to be more in line with the dynamic range generally expected of CT sensors. In addition, amorphous silicon matrix image detectors are subject to image lag, due to the phenomena of charge trapping in the amorphous material structure.

By operating the image detector 20 in a pulsed fluoroscopy mode and equipping it with an optical reset device 56 (FIG. 2), any residual image data (i.e. image lag) that may be left on the amorphous silicon matrix at the end of each frame is saturated out. Preferably, the optical reset device 56 is a brilliant light source mounted proximate the flat panel image detector 20, which light source, when momentarily flashed or energized, saturates out the residual image data from the previous image data acquisition. The optical reset device 56 is selectively triggered by the timing and control circuit 30 between successive image acquisitions.

It is contemplated that a number of smaller matrix image sensors, such as CCD detectors or small amorphous silicon flat panel imagers, can be tiled together in a mosaic fashion or a circle sector, rather than one large sensor. The image receptor 20 may also be equipped with a known x-ray anti-scatter grid to reduce the detection of radiation scattered from the patient body. It is also contemplated that a flat panel polysilicon image detector can be used in place of the amorphous silicon flat panel image detector 20.

The x-ray sensitivity of the flat panel imager 20 can be enhanced by depositing an x-ray absorbent layer of on top of the amorphous silicon. The layer may utilize direct x-ray detection, where x-rays are absorbed in a semi-conductor matrix, such as Selenium, Lead Sulfide, Cadmium Zinc Telluride, or Lead Iodide, and converted directly to electric charge, which is then accumulated by the amorphous Silicon matrix, or it may use indirect x-ray detection, where the x-rays are absorbed in a scintillating phosphor layer, such as Gadolinium Oxysulfide, Cesium Iodide, or Cadmium Tungstate, and converted to light, which is then absorbed and converted to electric charge in the amorphous Silicon matrix.

Figure 3:
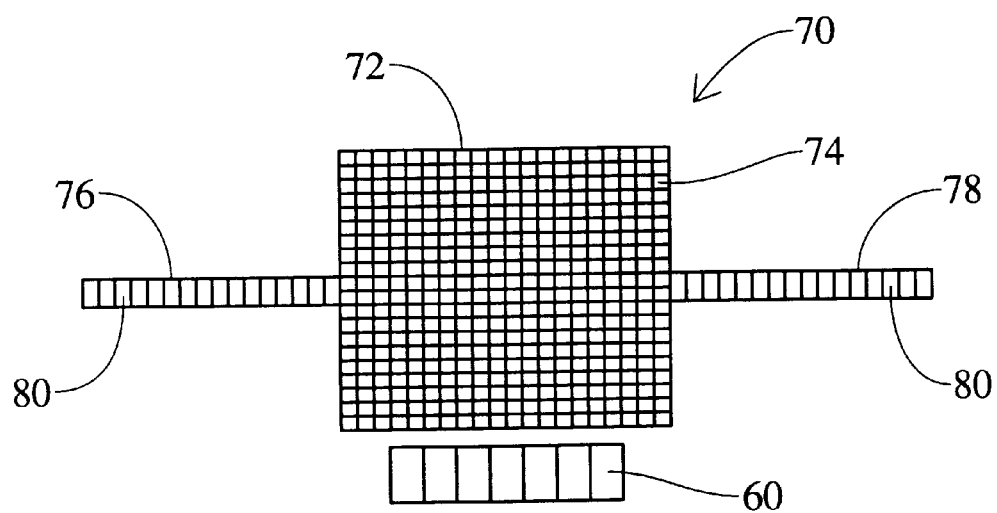
FIG. 3 is a diagrammatic view of an alternate flat panel image receptor associated with imaging apparatus of FIGS. 1 and 2.

The flat matrix image detector 20 may also include a known anti-scatter grid 58 mounted on a face of the detector 20 facing the x-ray source 18. The anti-scatter grid operates in a known manner to limit the x-rays that impinge upon the detector to those x-rays which have not been previously scattered by dense objects such as bone tissue. Alternatively, as shown in FIG. 3, a scatter detector 60 is placed outside the flat matrix image detector 20 to monitor the level of scattered x-rays which do not impinge upon the detector 20. The level of scattered x-rays detected by the detector 60 is then subtracted from the image data by the reconstruction processor 38 to eliminate or reduce the effects of scattered x-rays on the sensitivity of the detector 20.

It should be appreciated that the use of a rectangular cone beam results in better utilization of the x-rays generated in the x-ray tube 18. That is, because a thin fan beam is not utilized, less x-rays are discarded in the collimator 52, thereby improving the utilization of the x-rays generated. In addition, less long term power is dissipated in the x-ray tube 18 and the amount of energy that is accumulated in the tube per exam also is reduced. Thus, it is possible to use a smaller x-ray tube that runs under lower load conditions and having a significantly longer lifetime.

The radiation from the x-ray source 18 can be pulsed or continuous. Continuous radiation results in a simpler, less expensive system design, but precludes the use of an optical reset device in the sensor 20, thus introducing image artifacts due to the image lag characteristic of amorphous silicon flat panels. Pulsed radiation has the added advantage that the radiation pulses could be synchronized with, for example, the patient's heartbeat, thus freezing heart motion. In this embodiment, a cardiac monitor 62 sends cardiac signals to the timing and control circuit. Pulsing can be achieved either by using a pulsed high voltage generator connected to a conventional x-ray tube, or a constant high voltage generator connected to an x-ray tube equipped with a switching grid.

The reconstruction processor 38 can include means, such as an algorithm, to compensate the image data for image lag caused by the scintillator layer and the amorphous silicon matrix if an optical reset device is not used. The reconstruction processor 38 performs any image data corrections that are specific to the type of flat panel image receptor being used. In the case of an amorphous Silicon flat panel detector 20, this includes at least the following processes: pixel offset correction, pixel gain correction, defective pixel interpolation and blacklevel clamping (i.e. line correlated noise reduction).

Referring now to FIG. 3, a further flat panel image detector 70 includes a central, rectangular array 72 having a plurality of detectors 74, and wings 76, 78 each extending transverse from the array 72 and containing a plurality of additional detectors 80. The wing detectors 80 are used to at least partially compensate for the fact that the size (i.e., area) of the central array 72 is not large enough to acquire a full, non-truncated set of conventional CT data, i.e. to receive a complete set of image data across the entire object being imaged. More specifically, the wing detectors enable a full fan of data to be collected and reconstructed along the central slice. The portions of the central slice surrounding the region of interest are used to compensate for truncated artifacts in adjoining slices.

The detectors 80 sense or otherwise provide an approximate level of radiation attenuation data occurring in tissue outside the boundary of the imaged region. The attenuation data attributed to the tissue surrounding the region of interest is used to correct the attenuation values in the rays of adjoining slices. The corrected data is used in a reconstruction algorithm executed by the reconstruction processor 38 to acquire a truer volumetric image representation of the region of interest.

The imaging system of the present invention can be characterized as a fluoroscopic imaging system that has the capability of performing volume data acquisition in the same system. That is, the imaging system of the present invention can be configured as a radiography fluoroscopy, or interventional fluoroscopy system that also has a volume CT capability in the same system. The video processor 42 can retrieve individual projection images (i.e., fluoroscopic, radiographic, MIP) from the frame memory 36 for display on the monitor 44. The sequence of projection images from a rotary scan can be played back to the user in a fluoroscopy loop. The subjective appearance to the user is thus of a full three dimensional image, but that can only be spun around one axis.

However, it should be appreciated that the imaging system of the present invention can also be characterized as a volume CT system that has the capability of performing fluoroscopic imaging.

The invention has been described with reference to the preferred embodiment(s). Obviously, modifications and alterations will occur to others upon reading and understanding the preceding detailed description. It is intended that the invention be construed as including all such modifications and alterations insofar as they come within the scope of the appended claims or the equivalents thereof.

For instance, multiple sensors 20 and x-ray tubes 18 can be mounted around a stationary frame, with the x-ray tubes pulsed in sequence to emulate rotation. Each image sensor is enabled to acquire image data only when its opposing x-ray tube is pulsed. This eliminates the need for a rotating gantry and provides with real-time data acquisition enabling much shorter examination times. It is also contemplated to use multiple sensors mounted to a stationary frame and to place a single x-ray tube on a rotating frame.

Having thus described the preferred embodiment(s), the invention is now claimed to be:

1. A diagnostic imaging apparatus comprising:
   a gantry which supports an x-ray tube and a flat plate x-ray detector for rotation about an examination region with the x-ray tube and the flat plate detector disposed across the examination region from each other;
   a motor assembly for selectively rotating the x-ray tube and the flat plate detector around the examination region;
   a read out device for reading out a two dimensional array of data values from the flat plate detector, each data value being indicative of radiation attenuation along one of a plurality of diverging rays extending between the x-ray source and a sub-region of the flat plate detector;
   a reconstruction processor for reconstructing the data values read out during rotation of the x-ray tube and the flat plate detector around the examination region into a volumetric image representation;
   a video processor for (i) formatting the read out data values into appropriate format for display on a video monitor as a projection image and (ii) reformatting selective portions of volumetric image data into appropriate format for display on the monitor; and
   an optical reset device for saturating the flat plate x-ray detector after data values have been read out of the flat plate x-ray detector by the read out device.

2. The apparatus as set forth in claim 1 further including:
   a timing and control circuit for controlling the motor, the read out device, and an x-ray tube power supply, the timing and control circuit controlling (i) the motor to move the x-ray tube and flat plate detector around the examination region in steps, (ii) the x-ray tube power supply to pulse x-ray tube at each indexed step, and (iii) controlling the read out device to read out a frame of data after each indexed step.

3. The apparatus as set forth in claim 2 further including a physiological monitor for monitoring a reoccurring a physiological movement of the subject, the monitor being connected with the timing and control device for triggering the timing and control device to control the indexing of the steps in coordination with the monitored physiological movement.

4. The apparatus as set forth in claim 2 wherein the gantry includes a large diameter bearing having an inner race to which the x-ray tube and the flat plate detector are mounted and an outer race which is stationarily mounted, the motor rotating the inner race relative to the outer race.

5. The apparatus as set forth in claim 1 wherein the gantry includes a large diameter bearing having an inner race to which the x-ray tube and the flat plate detector are mounted and an outer race which is stationarily mounted, the motor rotating the inner race relative to the outer race.

6. A diagnostic imaging apparatus comprising:
   a gantry which supports an x-ray tube and a two-dimensional x-ray detector for rotation about an examination region, the x-ray tube and the x-ray detector positioned across the examination region from each other, the x-ray detector having at least one of an amorphous silicon layer and a polysilicon layer;
   a motor assembly for selectively rotating the x-ray tube and the x-ray detector around the examination region, the x-ray tube and x-ray detector cooperating to generate a plurality of two-dimensional arrays of data values during rotation around the examination region;
   a read out device for reading out the plurality of two dimensional arrays of data values from the x-ray detector, each data value being indicative of radiation attenuation along one of a plurality of diverging rays extending between the x-ray source and a sub-region of the x-ray detector;
   a timing and control circuit for controlling the motor, the read out device, and an x-ray tube power supply, the timing and control circuit controlling (i) the motor to move the x-ray tube and x-ray detector around the examination region in steps, (ii) the x-ray tube power supply to pulse the x-ray tube at each indexed step, and (iii) the read out device to read out a frame of data after each indexed step;
   a reconstruction processor for reconstructing the data values read out during rotation of the x-ray tube and the x-ray detector around the examination region into a three-dimensional volumetric image representation;

a volume image memory for storing the volumetric image representation;

a frame memory connected between the read out device and the reconstruction processor, the frame memory storing individual frames of data corresponding to the plurality of indexed steps around the examination region;

a video processor interconnected with the frame memory and the volume image memory for (i) formatting data values read out of the frame memory into appropriate format for display on a video monitor as projection images at any of a plurality of angular orientations and (ii) reformatting selective portions of volumetric image data into appropriate format for display on the monitor.

7. A diagnostic imaging apparatus comprising:

a gantry which supports an x-ray tube and a flag plate x-ray detector for rotation about an examination region, the x-ray tube and the flat plate detector positioned across the examination region from each other, the flat plate x-ray detector having at least one of an amorphous silicon layer and a polysilicon layer;

an adjustable collimator mounted adjacent the x-ray tube for adjusting a collimation of the emitted x-ray beam;

a mechanical drive for moving the flat plate detector closer to and further from the examination region;

a magnification control circuit for controlling adjustment of the collimator and the mechanical drive for the flat plate detector;

a motor assembly for selectively rotating the x-ray tube and the flat plate detector around the examination region, the x-ray tube and flat plate detector cooperating to generate a plurality of two-dimensional arrays of data values during rotation around the examination region;

a read out device for reading out the plurality of two dimensional arrays of data values from the flat plate detector, each data value being indicative of radiation attenuation along one of a plurality of diverging rays extending between the x-ray source and a sub-region of the flat plate detector;

a timing and control circuit for controlling the motor, the read out device, and an x-ray tube power supply, the timing and control circuit controlling (i) the motor to move the x-ray tube and x-ray detector around the examination region in steps, (ii) the x-ray tube power supply to pulse the x-ray tube at each indexed step, and (iii) the read out device to read out a frame of data after each indexed step;

a reconstruction processor for reconstructing the data values read out during rotation of the x-ray tube and the flat plate detector around the examination region into a three-dimensional volumetric image representation; and a video processor for (i) formatting the read out data values into appropriate format for display on a video monitor as a projection image and (ii) reformatting selective portions of volumetric image data into appropriate format for display on the monitor.

8. A diagnostic imaging apparatus comprising:

a gantry which supports an x-ray tube and a silicon-based detector for rotation about an examination region, the x-ray tube and the detector positioned across the examination region from each other, the detector having at least one of an amorphous silicon layer and a polysilicon layer;

an adjustable collimator mounted adjacent the x-ray tube for adjusting a collimation of the emitted x-ray beam;

a mechanical mechanism for moving the detector closer to and further from the examination region;

a magnification control circuit for controlling adjustment of the collimator and the mechanical mechanism for the detector;

a motor assembly for selectively rotating the x-ray tube and the detector around the examination region, the x-ray tube and detector cooperating to generate a plurality of two-dimensional arrays of data values during rotation around the examination region;

a read out device for reading out the plurality of two dimensional arrays of data values from the detector, each data value being indicative of radiation attenuation along one of a plurality of diverging rays extending between the x-ray source and a sub-region of the detector;

a reconstruction processor for reconstructing the data values read out during rotation of the x-ray tube and the detector around the examination region into a three-dimensional volumetric image representation; and a video processor for (i) formatting the read out data values into appropriate format for display on a video monitor as projection images and (ii) reformatting selective portions of volumetric image data into appropriate format for display on the monitor.

9. A method of diagnostic imaging, the method comprising:

a) rotating an x-ray tube and a flat plate detector which has a first sub-region including a central array of detectors and a second sub-region including at least one wing of detectors extending from the central array of detectors to a predetermined angular position about the examination region;

b) causing the x-ray tube to generate an x-ray radiation beam;

c) reading out a two-dimensional array of data values from the central array of detectors with each data value being indicative of radiation attenuation along one of a plurality of rays extending between the x-ray source and the first sub-region of the flat plate detector;

d) reading out additional data values from the flat plate detector with each additional data value being indicative of radiation attenuation along one of a plurality of rays extending between the x-ray source and the second sub-region of the flat plate detector;

e) repeating steps (a–d) a predetermined number of times to collect a plurality of two dimensional arrays of data values and a plurality of additional data values;

f) correcting the plurality of two-dimensional arrays of data values with the plurality of additional data values;

g) reconstructing the plurality of corrected two-dimensional arrays of data values into a volumetric image representation; and h) displaying at least a portion of the volumetric image representation on a monitor as a projection image.

10. A diagnostic imaging apparatus comprising:

a gantry which supports an x-ray tube and a flat plate x-ray detector for rotation about an examination region with the x-ray tube and the flat plate detector disposed across the examination region from each other, the flat plate x-ray detector including a central array of detectors and a plurality of additional detectors extending from said central array for collecting attenuation data outside an imaged region of said x-ray detector;

a motor assembly for selectively rotating the x-ray tube and the flat plate detector around the examination region;

a read out device for reading out a two dimensional array of data values from the flat plate detector, each data value being indicative of radiation attenuation along one of a plurality of diverging rays extending between the x-ray source and a sub-region of the flat plate detector;

a reconstruction processor for reconstructing the data values read out during rotation of the x-ray tube and the flat plate detector around the examination region into a volumetric image representation; and a video processor for (i) formatting the read out data values into appropriate format for display on a video monitor as a projection image and (ii) reformatting selective portions of volumetric image data into appropriate format for display on the monitor.

11. The apparatus as set forth in claim 10 wherein the projection image is a fluoroscopic projection image.

12. The apparatus as set forth in claim 10 wherein the projection image is a radiographic projection image.

13. The apparatus as set forth in claim 10 wherein the additional detectors extend along wings extending outward from the central array.

14. A method of diagnostic imaging with an imaging system including a gantry which supports an x-ray tube and a flat plate x-ray detector disposed across an examination region from each other, and a reconstruction processor for processing image data acquired by the flat plate x-ray detector which has at least one of an amorphous silicon and a polysilicon layer, the method comprising:

a) rotating the x-ray tube and the flat plate detector to a predetermined angular position about the examination region;

b) energizing the x-ray tube to generate an x-ray radiation beam;

c) reading out a two-dimensional array of data values from the flat plate detector with each data value being indicative of radiation attenuation along one of a plurality of diverging rays extending between the x-ray source and a sub-region of the flat plate detector;

d) repeating steps (a–c) a predetermined number of times to collect a plurality of two dimensional arrays of data values;

e) reconstructing the plurality of two-dimensional arrays of data values into a volumetric image representation;

f) displaying the volumetric image representation on a video monitor as a projection image;

g) varying a distance separating the x-ray tube from the flat plate detector to adjust a magnification level of the imaging system; and h) adjusting a collimator associated with the x-ray tube based on the distance separating the x-ray tube from the flat plate detector.

15. The method of claim 14, wherein step (a) includes:

i) rotating the x-ray tube and the flat plate detector at about 1° increments about the examination region.

16. The method of claim 14, wherein step (a) includes:

i) rotating the x-ray tube and the flat plate detector less that one full revolution about the examination region to generate the volumetric image representation.

17. The method of claim 14, wherein step (a) includes:

i) rotating the x-ray tube and the flat plate detector about the examination region at a rate of about 5 to about 90 seconds per revolution.

18. The method of claim 14, wherein step (d) includes:

i) repeating steps (a)–(c) about 3 to about 500 times.

19. The method of claim 14, wherein step (b) includes:

i) energizing the x-ray tube based on an output signal generated by a cardiac monitor.

20. The method of claim 14, further including:

i) displaying at least one of the two-dimensional arrays of data values on the video monitor as a two-dimensional image projection.

21. The method of claim 14, wherein step (f) includes:

i) displaying a portion of the volumetric image representation on a video monitor as a fluoroscopic projection image.

22. The method of claim 14, wherein step (f) includes:

i) displaying the volumetric image representation on a video monitor as a radiographic projection image.

23. A method of diagnostic imaging, the method comprising:

a) rotating a gantry supporting an x-ray tube and a flat plate detector to a predetermined angular position about an examination region;

b) causing the x-ray tube to generate an x-ray radiation beam;

c) reading out a two-dimensional array of data values from the flat plate detector with each data value being indicative of radiation attenuation along one of a plurality of diverging rays extending between the x-ray source and a sub-region of the flat plate detector, the flat plate detector having at least one of an amorphous silicon layer and a polysilicon layer;

d) repeating steps (a–c) a predetermined number of times to collect a plurality of two dimensional arrays of data values;

e) reconstructing the plurality of two-dimensional arrays of data values into a volumetric image representation;

f) displaying at least a portion of the volumetric image representation on a video monitor as a MIP projection image.

24. A diagnostic imaging apparatus comprising:

a gantry which supports an x-ray tube and a flat panel x-ray detector for rotation about an examination region with the x-ray tube and the flat panel detector disposed across the examination region from each other;

a motor assembly for selectively rotating the x-ray tube and the flat panel detector around the examination region;

a read out device for reading out a two dimensional array of data values from the flat panel detector, each data value being indicative of radiation attenuation along one of a plurality of rays extending between the x-ray source and a sub-region of the flat panel detector;

a reconstruction processor for reconstructing the data values read out during rotation of the x-ray tube and the flat panel detector around the examination region into a volumetric image representation;

a video processor for (i) formatting the read out data values into appropriate format for display on a video monitor as a maximum intensity projection (MIP) image and (ii) reformatting selective portions of volumetric image data into appropriate format for display on the monitor.

25. A method of diagnostic imaging, the method comprising:
   a) rotating an x-ray tube and a flat plate detector which has a first subregion and a second subregion to a predetermined angular position about the examination region;
   b) causing the x-ray tube to generate an x-ray radiation beam;
   c) reading out a two-dimensional array of data values from the flat plate detector first subregion with each data value being indicative of radiation attenuation along one of a plurality of rays extending between the x-ray source and the first subregion of the flat plate detector;
   d) reading out additional data values from the flat plate detector second subregion with each additional data value being indicative of radiation attenuation along one of a plurality of rays extending between the x-ray source and the second subregion of the flat plate detector;
   e) repeating steps (a–d) a predetermined number of times to collect a plurality of two dimensional arrays of data values and a plurality of additional data values;
   f) correcting the plurality of two-dimensional arrays of data values with the plurality of additional data values;
   g) reconstructing the corrected two-dimensional arrays of data values into a volumetric image representation;
   h) displaying a selected portion of the volumetric image representation on a monitor.

26. A method of diagnostic imaging, the method comprising:
   a) rotating an x-ray tube and a flat plate detector to a predetermined angular position about the examination region;
   b) causing the x-ray tube to generate an x-ray radiation beam across the examination region;
   c) reading out a two-dimensional array of data values from the flat plate detector with each data value being indicative of radiation attenuation along one of a plurality of diverging rays extending between the x-ray source and a sub-region of the flat plate detector;
   d) repeating steps (a–c) a predetermined number of times to collect a plurality of two dimensional arrays of data values;
   e) reconstructing the plurality of two-dimensional arrays of data values into a volumetric image representation;
   f) displaying the volumetric image representation on a monitor as a projection image; and
   g) saturating the flat plate detector with an optical reset device after reading out the two-dimensional array of data values.

27. The method of claim 26, wherein the flat plate detector includes at least one of an amorphous silicon layer and a polysilicon layer.

* * * * *